United States Patent [19]

Shi

[11] Patent Number: 4,991,590
[45] Date of Patent: Feb. 12, 1991

[54] FIBER OPTIC INTRAVASCULAR BLOOD PRESSURE TRANSDUCER

[75] Inventor: Weimin Shi, Piscataway, N.J.
[73] Assignee: Martin Goffman Associates, Edison, N.J.
[21] Appl. No.: 303,847
[22] Filed: Jan. 30, 1989
[51] Int. Cl.⁵ .............................................. A61B 5/0215
[52] U.S. Cl. ........................................ 128/667; 128/675; 128/748; 73/705; 73/715
[58] Field of Search ............... 128/665, 666, 667, 672, 128/673, 675, 748, 634; 356/41; 73/705, 715

[56] References Cited

U.S. PATENT DOCUMENTS

| | | | |
|---|---|---|---|
| 3,273,447 | 9/1966 | Frank ................................ | 128/675 |
| 3,946,724 | 3/1976 | LaBalme .......................... | 128/675 |
| 4,030,485 | 6/1977 | Warner ............................ | 128/667 |
| 4,611,600 | 9/1986 | Cohen ............................. | 128/667 |
| 4,682,895 | 7/1987 | Costello .......................... | 128/634 |
| 4,718,423 | 1/1988 | Willis et al. .................... | 128/634 |

OTHER PUBLICATIONS

Matsumoto et al., "The Development of a Fibre Optic Catheter Tip Pressure Transducer", vol. 2, No. 5, pp. 239-242, J. Med. Eng. and Technol. (GB), Sep. 1978.
Lekholm et al., "Optoelectronic Transducer for Intravascular Measurements of Pressure Variations", vol. 7, pp. 333-335, Med. and Biol. Engng. (GB), Nov. 1968.

Primary Examiner—Kyle L. Howell
Assistant Examiner—K. M. Pfaffle
Attorney, Agent, or Firm—Spencer & Frank

[57] ABSTRACT

A device for the measurement of the blood pressure of a patient includes an arrangement for transmitting a light through an optical fiber; an arrangement for receiving and measuring a reflected light through an optical fiber; and a cylindrically shaped pressure sensor having a side window and a plate having two sections which moves in accordance with the applied blood pressure thereby causing the reflection and detection of different amounts of light based on the applied blood pressure at the window.

20 Claims, 6 Drawing Sheets

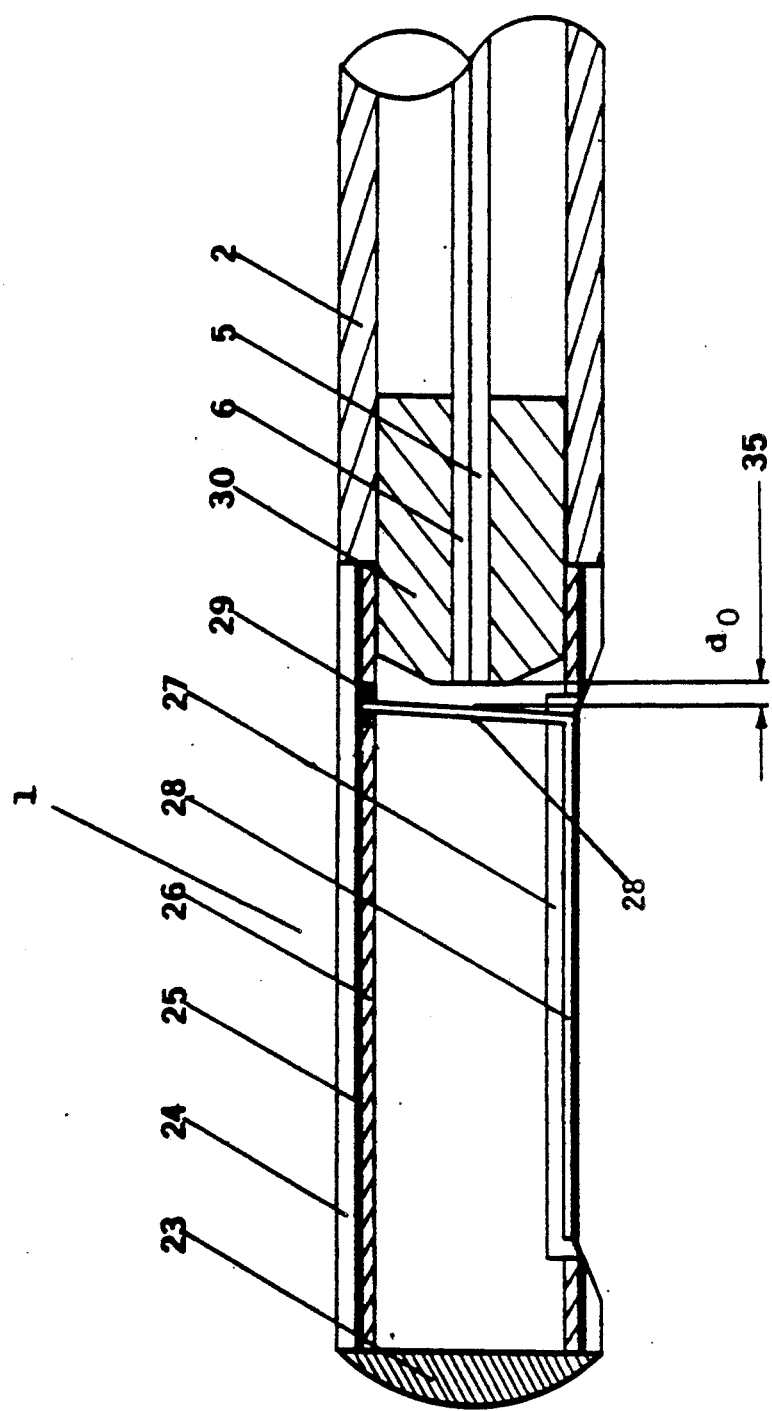

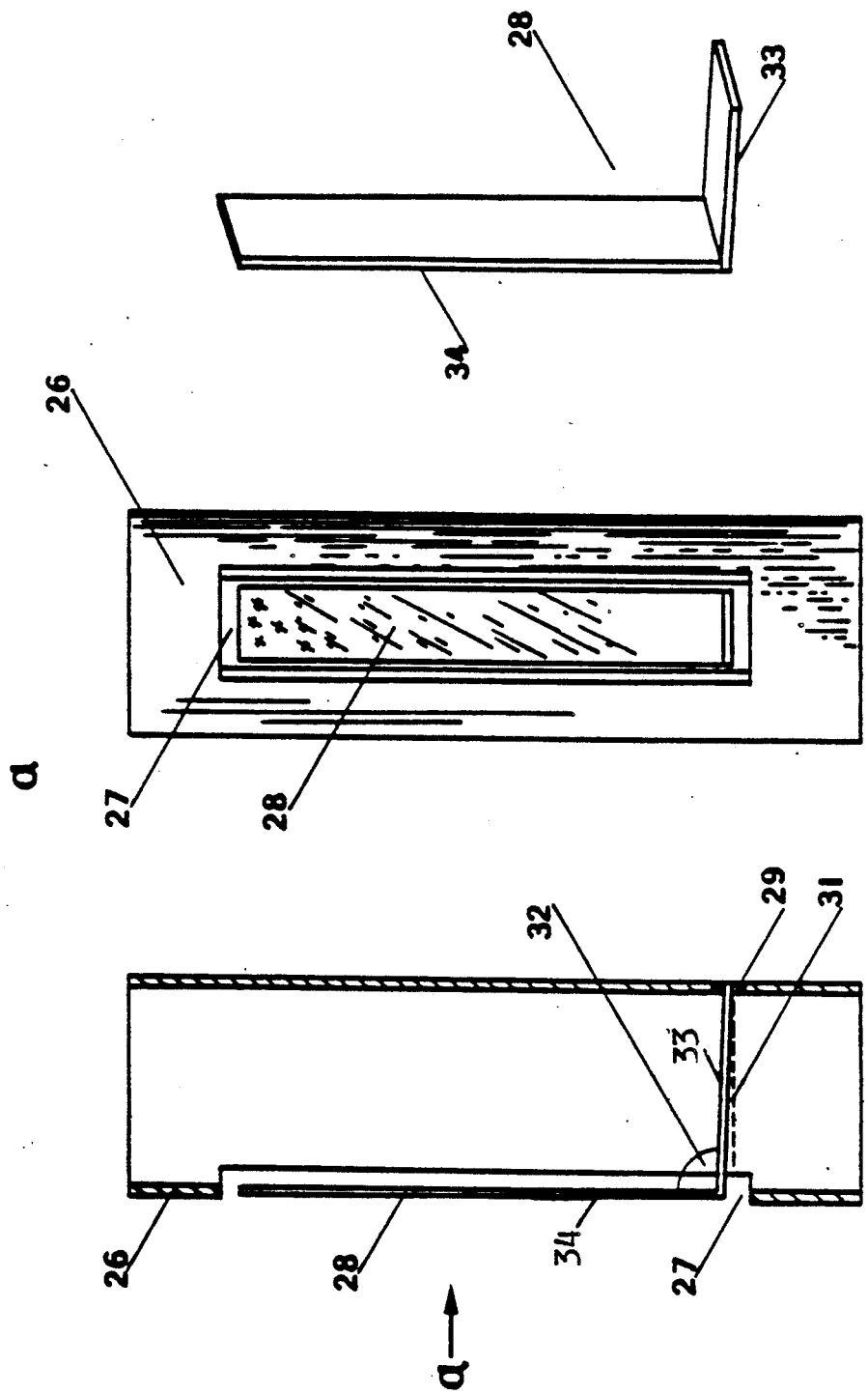

FIBER OPTIC INTRAVASCULAR BLOOD PRESSURE TRANSDUCER

BACKGROUND OF THE INVENTION

The measurement of blood pressure is one of the oldest arts in the field of medicine, dating back some 350 years. Today, the measurement of blood pressure can be done both indirectly, by use of a sphygmomanometer, or directly by means of a device which is in direct contact with the circulatory system. The former is the most common in routine physical examinations, and the latter the most commonly used blood pressure device during specialized surgical procedures. The instant invention relates to a direct method of measuring a patient's blood pressure using a fiber optic intravascular transducer during surgery or in a routine catheterization test.

Before the introduction of fiber optic technology in the 1960's and 1970's, there were two principal types of devices developed for direct blood pressure measurements. These types of devices have been in use in hospitals since then without any major improvements in the art of direct blood pressure measurement.

The first type of device is a so called fluid-filled catheter manometer. It is composed of two basic parts; a hollow catheter and a pressure sensor. According to this type of device, the catheter is filled with a saline solution and then introduced into a blood vessel while the pressure sensor is placed outside the patient's body. The fluid filled catheter provides a hydraulic connection between the source of the vascular blood pressure and the sensor element.

This hydraulic pressure transmission system with its external sensor is relatively simple, durable, flexible and inexpensive. However, inherent in this device are a number of problems in the measurement of vascular blood pressure.

First, the nature of the saline solution and the flexible catheter wall material yield very poor dynamic performance of the system. A typical resonant frequency of 15-20 Hz, far below the minimum required 40-50 Hz, plus a non-optimal damping factor, cause distortion in the measured blood pressure waveforms. Second, the liquid-coupling system needs to be flushed at regular intervals to avoid blood clotting at the catheter tip. Thus, long-term measurements cannot be made with this device. Third, any bubbles existing in the fluid-filled system will not only degrade the measurements of blood pressure, but will also remain lethal threats to the patient's life. Finally, artifacts are often produced due to body motion, the relative large mass of the fluid column, and relative long transmission distance for blood pressure.

Many of the above problems associated with a fluid-filled catheter are eliminated by use of the second type of device which makes use of a semiconductor pressure sensor at the catheter tip. The prime advantage of the semiconductor catheter-tip blood pressure transducer is that the measurement of vascular pressure is made at the same place where it occurs rather than relying on the fluid coupling system to transmit pressure to an external sensor.

Although it produces artifact-free performance, the semiconductor catheter-tip pressure transducer continues to have other unsolved problems. Because of the electrical connection between the patient's body and the electronic device, a risk is imposed to the patient's health by possible excessive electrical current leakage which can disturb the normal electrophysiology of the heart. This can lead to the onset of cardiac arrhythmia and electric shock. This risk of cardiac arrhythmia and electrical shock is one of the medical profession's major concerns with the semiconductor type of catheter-tip transducer. In addition, the complicated construction causes this type of transducer to be a high cost product, which renders it impractical as a disposable device. Moreover, the multiple use of this type of a transducer not only consumes a great deal of labor time to maintain the transducer but also introduces possible cross contamination problems.

The development of fiber optic technology has solved many of the problems that existed in prior direct blood pressure measurement devices. A device employing fiber optic technology is capable of performing as well as a semiconductor catheter tip pressure sensor, and at the same time eliminates the two major problems associated with the semiconductor device, electrical leakage and cross contamination.

The work on fiber optic catheter-tip blood pressure transducers started in the 1960's. In a typical early model of a fiber optic catheter tip pressure transducer, a pressure sensitive membrane is mounted at the catheter tip where an end opening is made to allow the direct contact of the membrane to the measured blood pressure. Right behind the membrane is an optical fiber bundle which stays inside the catheter. At the proximal end, the fiber bundle bifurcates into two legs connected to a light source and a light detector, respectively. Light from the light source is transmitted through those fibers associated with that leg of the bundle and then reaches the pressure sensitive membrane with light reflecting properties. Part of the reflected light is collected by those fibers in the bundle which go to the light detector and is transmitted back to the detector. At the distal end, all of these fibers are made part of a single bundle. When a pressure is applied and coupled through the end opening at the catheter tip to the membrane, the intensity of the reflected light will be altered by the displacement of the membrane. Thus, the signal generated by the light detector will be changed in direct proportion to the applied pressure. The pressure signal is then processed and displayed (or recorded).

There are at least two problems associated with this type of fiber optic transducer, and both are related to the end opening at the catheter tip. The placement of the pressure detection means at the distal end opening subjects the pressure measurement to a source of error. When introduced into the blood stream, the catheter is parallel to the direction of the blood flow. The end opening of the catheter faces either the upstream or down stream flow of blood. In this arrangement, based on Bernoulli's law, the total measured pressure will be the static blood pressure plus or minus the kinetic energy pressure. The static blood pressure is the desired parameter and the kinetic energy pressure is the introduced error. This error may be as large as 10% of measured pressure when the patient is at rest or 50% when the patient is in an active state. In addition to the measurement error, the edges at the catheter tip necessary with this type of configuration will compound thrombus formation.

To overcome the above problems associated with the end opening at the catheter tip, two types of fiber optic catheter pressure sensors having a side opening at the catheter tip are reported in a 1978 article entitled "The Development of Fiber Optic Catheter Tip Pressure Transducer", Journal of Medical Engineering and Technology, Vol. 2, No. 5, by H. Matsumoto & M. Saegusa, and disclosed in 1987 U.S. Pat. No. 4,691,708 entitled "Optical Pressure Sensor for Measuring Blood Pressure" of J. Kane.

In Matsumoto's disclosure, a membrane to cover the side opening at the catheter tip and a cantilever are responsive to applied pressure. The displacement of the whole structure causes movement of a mirror which is mounted at the end of the cantilever. The position of the mirror will alter the active reflection surface available for the inlet light transmitted by fiber optic means extending the length of the catheter so that the produced pressure signal at the light detector is in direct proportion to the static blood pressure. However, it is extremely difficult to precisely determine the initial position of the micro-mirror relative to the distal end of the optical fibers. A very slight misalignment between them will destroy the sensor's performance completely.

In Kane's patent, a pressure transducer is located at the distal end of the catheter and includes a fixed mirror which is spaced forward of the distal end of the single optical fiber. This mirror is fixed in position relative thereto, so as to receive and reflect light emitted from the distal end of the optical fiber and back into the distal end thereof. A side port is provided in the catheter housing adjacent to its distal end, which is sealed with a plastic membrane responsive to pressure acting transversely thereof. The plastic membrane is coupled to the distal end of the optical fiber through a wedge-shaped bias support. Under the influence of the applied pressure, the distal end of the fiber is displaced, thus changing the amount of reflected light.

There a number of problems with Kane's transducer. First, it ignores the initial distance and angle between the distal end of the optic fiber and the fixed mirror. Misplacement of these two parameters will sacrifice greatly the transducer's sensitivity, dynamic range and linearity. The transducer structure provides no means to accurately and precisely preset and trim the initial distance and angle between the distal end of the optic fiber and the fixed mirror. This will cause extreme difficulty in maintaining reproducibility in the sensor's performance. In addition, both static and dynamic pressure impacts can deform its flexible structure to some extent because metal is not employed to increase the strength of the pressure sensor. This can change the above two parameters thus introducing significant artifacts into pressure measurements. Secondly, the plastic membrane used has poor frequency response and large hysteresis which can cause distortion in measured pressure waveforms. The pressure deformation of plastic material also produces significant baseline shift. Finally, this transducer needs a very expensive means to convert the one fiber used into the two legs connected to the light source and the light detector. Thus, Kane's design has not proven to be practically useful.

SUMMARY OF THE INVENTION

It is an object of the present invention to provide physicians with a novel fiber-optic intravascular transducer for the direct measurement of the blood pressure of a patient during surgery or in a catheterization test.

It is yet another object of the present invention to provide a fiber optic intravascular transducer having a unique optical, mechanical, and electronic design which overcomes the problems and limitations associated with prior devices used for direct blood pressure measurements.

These and other objects are achieved by the direct blood pressure measurement device according to the present invention which comprises a disposable fiber optic catheter tip blood pressure transducer and a pressure signal processing unit. In accordance with the invention, the pressure transducer comprises a pressure sensor mounted at the catheter tip for insertion into a blood vessel during blood pressure measurement, a catheter housing optical fibers for light transmission, and an opto-electronic box at the proximal end of the catheter.

The catheter acts to provide mechanical protection to the optical fibers inside the catheter and guidance for transducer insertion. The optic fibers inside the catheter are terminated in a piece of strong, rigid tubing, preferably metal or hard plastic, which is connected to another rigid shell, e.g., metal, which contains a leaf or plate mounted therein. The rigid shell is covered with a watertight silicon membrane (or other suitable plastic membrane) which is exposed to the blood.

The leaf comprises two sections bent at an angle of approximately 90° one section to the other. One section has its end cemented into or otherwise attached to a slit or fitting in the wall of the shell. This section serves as a reflector adjacent to the tip of the optic fibers. The other section faces a side window in the shell. The leaf structure is preferably metal but can be any semi-flexible material having a reflective surface.

The vascular blood pressure is applied through the side window of the shell thereby displacing the metal leaf an amount consistent with the amount of blood pressure applied through the window. The angled section of the metal leaf will convert its transverse displacement into a longitudinal displacement of the reflection section of the metal leaf, thus changing the distance between that section of the metal leaf and the tips of the optical fibers.

At the proximal end of the catheter tip, the two optic fibers are separated, one coupled directly to a light source and the other to a light detector. The carrier light from the light source is transmitted by the transmitting fiber and is emitted onto the metal leaf reflector section. The changes in the distance between the reflector portion of the metal leaf and the tips of the optic fibers vary in accordance with the applied blood pressure and will modulate the intensity of the light reflected by the reflector and received by the receiving fiber. Thus, the output pressure signal from the signal processing unit is in direct proportion to the measured blood pressure.

BRIEF DESCRIPTION OF THE DRAWINGS

FIG. 3 is a cross section of the distal part of the catheter having a pressure sensor mechanism at its tip.

FIG. 4 is a cross section of the metal shell and metal leaf structure of the invention.

FIG. 5 is a top view of the shell and leaf structure of the invention.

FIG. 6 is a perspective view of the leaf structure.

DETAILED DESCRIPTION OF THE INVENTION

Figure 1:
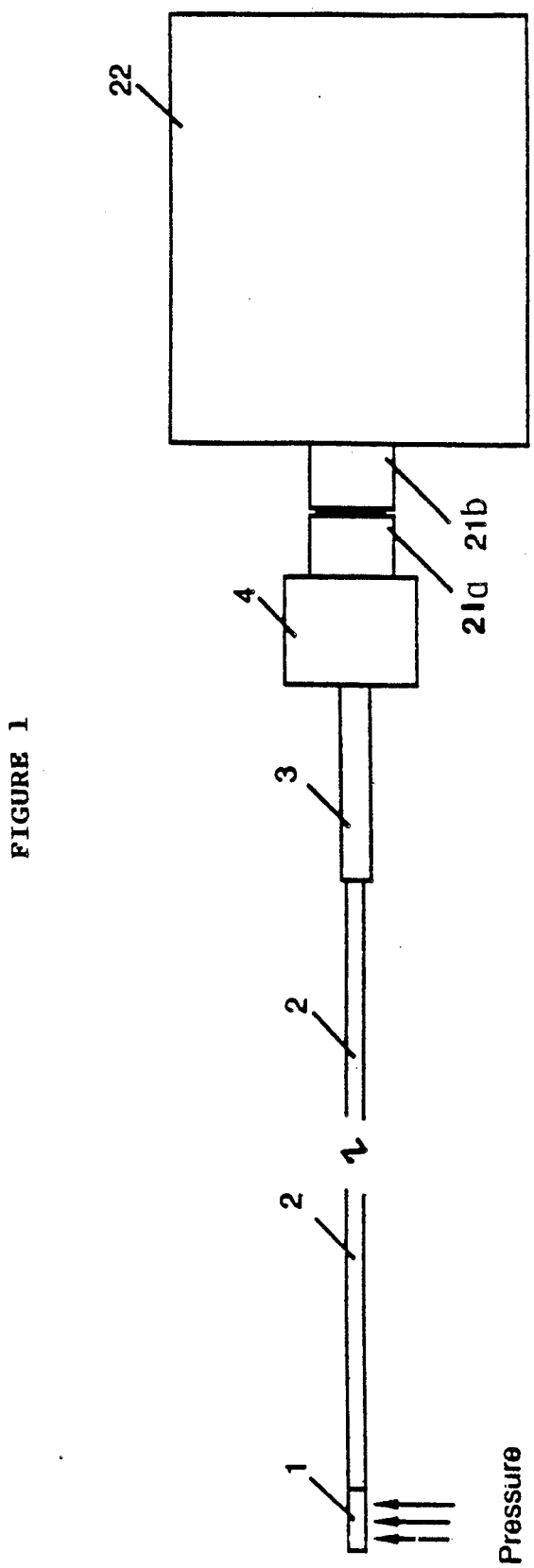
FIG. 1 is a diagram of the device according to the invention for direct measurement of intravascular blood pressure.

FIG. 1 shows a device according to the invention useful for intravascular blood pressure measurement, which comprises a catheter tip blood pressure transducer and a signal processing unit. The catheter tip blood pressure transducer may be disposable. During blood pressure measurement, the catheter-tip pressure sensor mechanism (1) and the segment (maximum up to 120 cm in length) of the catheter (2) will be inserted into the blood circulation system through an appropriate superficial blood vessel and advanced to the site where the blood pressure data is desired. The fiber optic reflective type pressure sensor mechanism (1) is incorporated at the tip (distal end) of the standard cardiac catheter (2). The proximal end of the catheter (2) is attached, e.g., cemented to an opto-electronic box (4) having a plastic tubing (3) to protect and increase the strength of this connection. Through the multi-pin connector (21a male) and (21b female) the opto-electronic box (4) is coupled to the signal processing unit (22).

Figure 2:
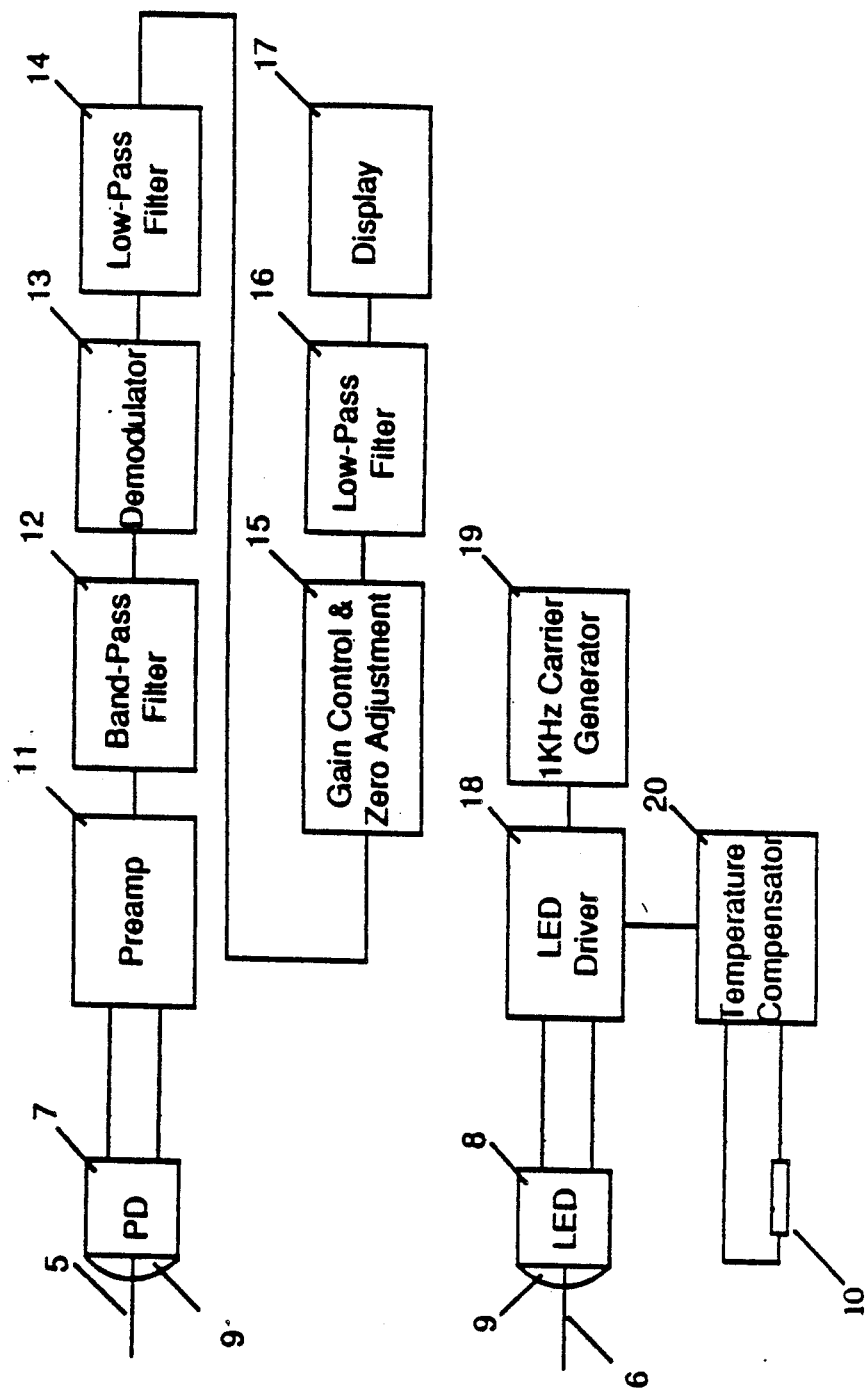
FIG. 2 is another diagram of the device according to the invention.

With reference to FIG. 2, upon power onset, the carrier signal of 1 kHz is produced in the 1 kHz carrier generator (19) and is input into the light source LED (light emitting diode) driver (18). The LED driver (18) provides the light source LED (8) with a driving current of the desired intensity. A thermistor (10) and a temperature compensator (20) are used to compensate for the unwanted temperature effects of the emission intensity of the light source LED (8). A corresponding signal response to any changes in local temperature will be generated to regulate the light source driving current, thus resulting in a temperature-effect-free light emission intensity of the light source LED (8). The carrier light from the light source LED (8) is directly injected into the optical fiber (6) housed by the cardiac catheter (2), and sent to the pressure sensor (1) located at the proximal end of the catheter (2), as depicted in FIG. 1. A portion of input carrier light will then be reflected by the sensor component, i.e., the reflector section of the metal leaf, and received by another optic fiber (5). When blood pressure is applied, the light reflectivity of the catheter tip pressure sensor mechanism (1) will be changed in response to the instantaneous pressure. Thus, the intensity of the reflected carrier light will be in accordance with the measured blood pressure. At the proximal end of the catheter (2), the carrier light collected by the optic fiber (5) is directly coupled to a photodetector PD (7). This signal is amplified by a preamplifier (11), band-pass filtered by a band-pass filter (12), demodulated by a demodulator (13), and then low-pass filtered by a low-pass filter (14). The gain and reference zero level of the pressure signal will be adjusted by gain and zero control (15). After a one stage low-pass filter (16), the measured blood pressure signal is sent into a display/record stage (17).

As displayed in FIG. 2, a carrier light signal of 1 KHz instead of a DC light signal, is preferred. This is to eliminate any existing electromagnetic noise interfering with the normal measurement, thus resulting in a better signal to noise ratio.

The use of the disposable opto-electronic box (4) (FIG. 1) provides a simple, inexpensive and reliable connection between the blood pressure transducer and the signal processing unit. It eliminates the problems associated with the coupling of the optical fibers to the opto-electronic devices (light source and detector) used by prior devices. These problems include high cost, low reproducibility and poor reliability.

Two optic fibers are utilized in the invention instead of only one single fiber as used in other devices. This significantly simplifies the optical and mechanical structure of the transducer because of the elimination of an expensive and lower effective beam splitting system or light coupling system to distinguish the input and output light signals.

The selection of the size of the optic fiber is important in determining the sensor's sensitivity and dynamic range. If higher sensitivity but smaller dynamic range is expected, the use of fibers with smaller diameter is suggested. The preferred range of fiber diameter is between about 40 um/50 um (core/cladding) to 400 um/500 um (core/cladding).

The sizes of cardiac catheters preferred for use in the invention range from about 2 French up to 8 French. The pressure sensor incorporated at the catheter tip should have the same size. Because of the free opening at the proximal end of the catheter (2) into the opto-electronic box (4) (FIG. 1), the ventilation of the catheter to the atmosphere is achieved automatically. Therefore, at the catheter tip pressure sensor mechanism, the measured blood pressure is relative to the atmospheric pressure.

An unacceptable long-term stability is associated with some previous fiber optic transducers. The thermal and aging effects of the light source LED is the major contributor to this problem. In the device according to the invention, the thermal effect of the light source LED is overcome by a thermistor adjacent to the LED to monitor the local temperature variation and a temperature compensator to adjust the LED driving current accordingly. The aging effect of the LED is avoided by discarding the LED with the transducer, which may be disposable, after a single use. This minimizes or eliminates the aging effect.

FIGS. 3-7 demonstrate the invention in greater detail. FIG. 3 shows the structure of the pressure sensor mechanism (1) incorporated at the tip of the catheter (2). The pressure sensor (1) is basically made up of the shell (26), which is preferably metal, the metal leaf (28), and a fiber holder (30). The shell (26) and metal leaf or plate structure (28), which may be pre-assembled, is shown in FIG. 4. The metal shell (26) is preferably a piece of thin-wall metal tubing. The high mechanical strength of the metal tubing will protect the sensor unit from any mechanical deformation caused by pressure impact. The metal shell (26) contains a side window (27) as shown in FIGS. 3, 4, and 5.

Facing the side window, in the opposite side wall of the metal shell (26), there is a tiny rectangular slit (29). With reference to FIGS. 4 and 6, the metal leaf (plate) (28) is a rectangular thin metal plate which is bent into two sections (33 and 34) with a bending angle (32) about 90°, and preferably slightly larger than 90°. The leaf is preferably made of metal, but may be any semi-flexible material having a reflective surface. The dimension of the section (34) of the metal leaf (28) is very close to that of the side window (27) in the wall of the metal shell (26) and can be moved into the inside of the metal shell (26) freely. The reflector portion (33) of the metal leaf (28) is cemented or otherwise affixed in slit (29). The other section (34) of the metal leaf (28) stands in front of the side window (27), as shown in FIG. 5.

With further reference to FIG. 3, the optic fibers (5) and (6) are terminated in a fiber holder (30) which is a piece of a metal (or hard plastic) column with an outside diameter the same as the inside diameters of the metal shell (26) and catheter (2). Approximately half of the fiber holder (30) will be inserted into the catheter (2). The other end of the fiber holder (30) is situated in the metal shell (26) and advanced to the position which keeps the tips of the optic fibers (5) and (6) and the reflector surface of the metal leaf reflector section (33) a distane $d_0$ (35) apart. The distance $d_0$ (35) is called the initial distance, which is critical to determine the sensitivity and dynamic range of the pressure sensor (1). The surface of the metal leaf section (33) facing the optic fibers serves as a highly reflective reflector.

After the distance $d_0$ (35) is determined, the fiber holder (30) and metal shell (26) are cemented together or otherwise affixed into an entire structure. A waterproof, highly stretchable and mechanically strong silicon rubber membrane (25) or other suitable plastic material is used to seal the metal shell (26) against blood leakage and transmits the blood pressure to the metal leaf (28). The metal leaf section (34) is cemented or otherwise affixed to the shell. The distal tip of the metal shell (26) is sealed with a smoothly curved plastic potting compound (23). The sensor unit is finished with a thin plastic coating (24) formed over its entire surface except the side window (27). Both the smoothly curved plastic potting compound (23), and plastic coating (24), help to avoid problems with blood coagulation.

Figure 7:
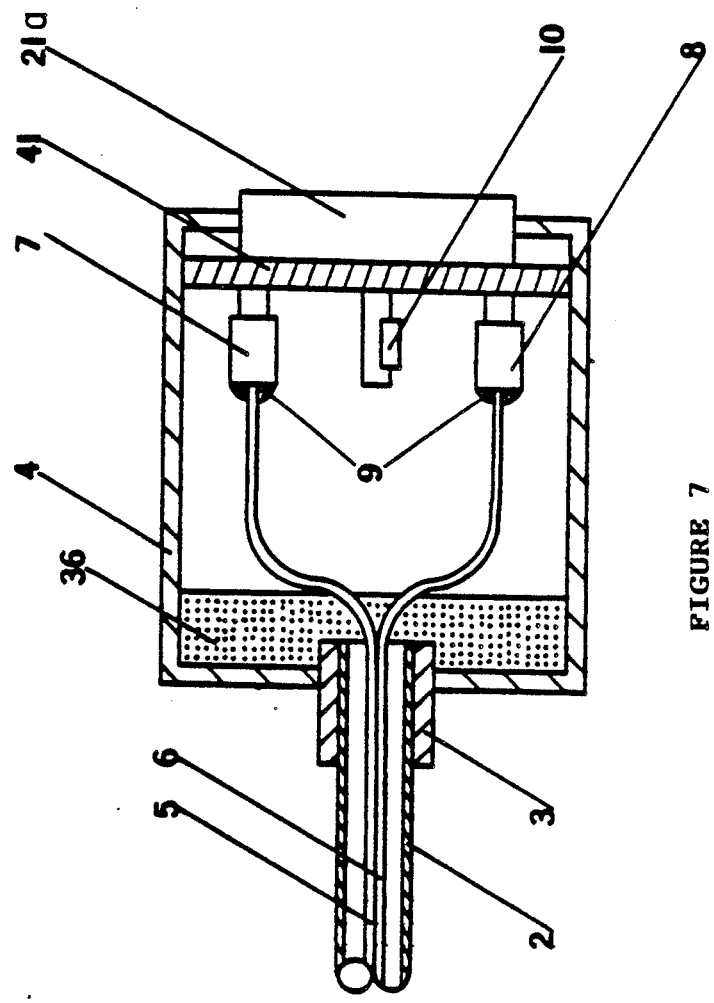
FIG. 7 is a cross section of the proximal part of the catheter which connects directly to the opto-electronic box housing the light source and the light detector.

FIG. 7 is an enlarged longitudinal sectional view of the proximal end of the catheter (2) and the opto-electronic box (4). In one embodiment of the invention, the catheter (2) is directly fused into the opto-electronic box (4) by means of cement compound (36). A plastic jacket (3) is used to increase the strength of the connection between the catheter (2) and the opto-electronic box (4). Optic fibers (5 and 6) are directly coupled to the photodetector PD (7) and light source LED (8) respectively. Both the photodetector PD (7) and the light source LED (8) are devices without a dome lens in construction. Application of epoxy cement (9) is preferably used to ensure this coupling and to maintain its mechanical strength. The thermistor (10) monitors the temperature variation inside the opto-electronic box (4) and signals the temperature compensator circuitry in the signal processing unit to correct the temperature effects of the light source LED (8). The photodetector PD (7), the light source LED (8) and the thermistor (10) are mounted on a IC board (41). The opto-electronic box (4) is linked to the pressure signal processing unit (22) by the male multi-pin connector (21a) and female multi-pin connector (21b).

With further reference to FIGS. 3 and 4, the side window in the metal shell (26) allows the transverse coupling of the measured blood pressure to the sensing mechanism or metal leaf (28) located inside the metal shell (26), thus eliminating measurement error introduced by kinetic energy. The measured pressure will then cause the transverse displacement of the section (34) of the leaf structure (28). Through the angled structure, the transverse movement of the metal leaf section (34) will introduce the longitudinal displacement of the metal leaf reflector section (33), thus changing the distance between the metal leaf reflector section (33) and the tips of optic fibers (5 and 6) in fiber holder (30). The directional angle (31) is set to ensure the direction of the longitudinal displacement of the metal leaf reflector section (33).

Figure 8:
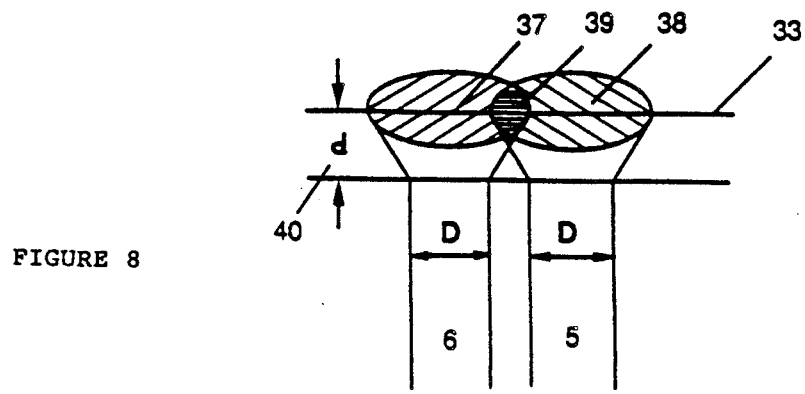
FIG. 8 is an illustration of the light transmitting and receiving optic fibers and the light reflecting geometry of the reflector section of the leaf structure.
Figure 9:
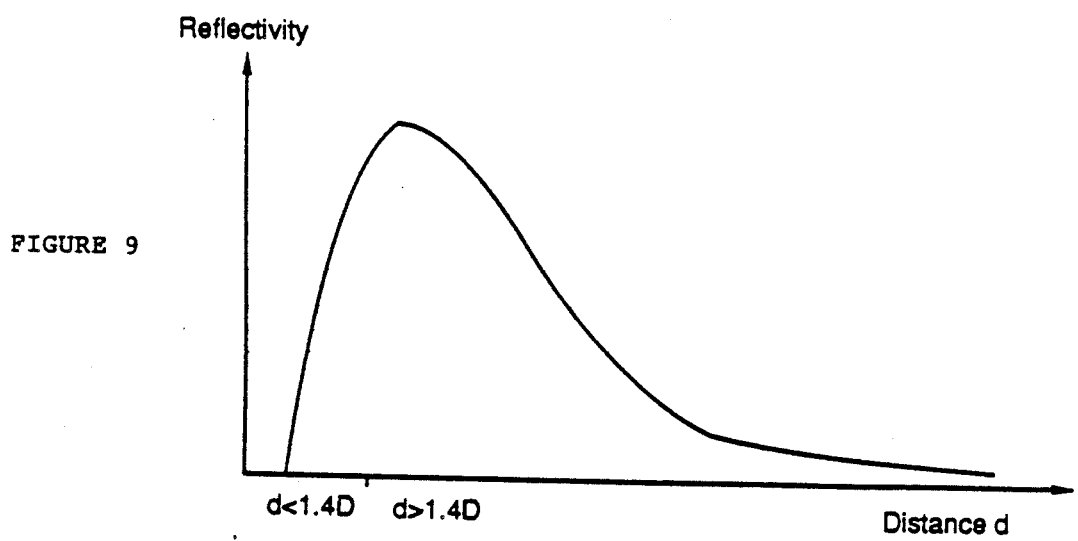
FIG. 9 is an illustration demonstrating the principle of the fiber optic pressure measurement.

As shown in FIGS. 8 and 9, the carrier light is emitted from the light transmitting optic fiber (6) and projects a circle (37) on the reflective surface of the metal leaf section (33). The projection circle (37) shares an overlap area (39) with another circle (38) projected by the light receiving optic fiber (5). Only the light projected into the overlap area (39) by the optic fiber (6) can be received by the optic fiber (5). The light reflectivity of the sensor is defined as the ratio of the intensity of the light reflected by the metal leaf reflector section (33) and collected by the optic fiber (5) to the intensity of the light transmitted by the optic fiber (6) and received by the metal leaf section (33). The sensor's reflectivity can then be calculated as the ratio of the overlap area (39) to the projection circle area (37). When the distance d (40) between the tips of optic fibers (5 and 6) and the reflective surface of the metal leaf section (33) changes, based on simple geometry, both the areas of the overlap (39) and the projection circle (37) will change. When the distance d (40) is smaller than about 1.4 times the diameter D of the optic fibers, relative changes in the overlap area (39) is larger than that of the projection circle area (37). Thus the sensor's reflectivity follows the changes in the distance d (40) in the same direction, which is the response to the measured blood pressure. At the signal processing unit (22) a signal dependent upon the measured blood pressure will be processed and recorded.

While there have been described what are presently believed to be the preferred embodiments of the invention, it will be apparent to one skilled in the art that numerous changes can be made in the structure, ingredients, proportions and conditions set forth in the foregoing embodiments without departing from the invention as described herein and as defined in the appended claims.

What is claimed is:

1. A device for the measurement of the blood pressure of a patient which comprises:
   (a) means for producing a light for transmission through an optical fiber;
   (b) means for receiving and measuring the light reflected through an optical fiber;
   (c) a fiber holder;
   (d) a first optical fiber for the transmission of the produced light having a distal end arranged longitudinally in said fiber holder and a proximal end connected to the means for producing a light;
   (e) a second optical fiber for the transmission of the reflected light having a distal end arranged longitudinally in said fiber holder and a proximal end connected to the means for receiving and measuring a reflected light;
   (f) a pressure sensing mechanism connected to said fiber holder comprising a cylindrically shaped outer shell having a side window; and a thin plate having two sections including a reflector section arranged at an angle of approximately 90° to the other section, said other section being movably situated within said window and one end of the reflector section being attached to the outer shell opposite to said window, said reflector section of said plate being located a predetermined nominal distance from and perpendicular to the distal end of said optical fibers such that the reflector section reflects light emitted from the first optical fiber into the second optical fiber in dependence of a variation in distance between the reflector setion and the distal ends of said optical fibers; and (g) a membrane surrounding said shell to seal the pressure sensing mechanism blood and to permit the transmission of the blood pressure to the plate.

2. The device according to claim 1 wherein the means for producing a light includes a light source, a thermistor mounted in proximity to said light source and a temperature compensator coupled to said light source and said thermistor for compensating for effects of temperature changes on the intensity of the light produced by said light source.

3. The device according to claim 2, wherein said means for receiving and measuring a light includes a light detector, and said device further includes a housing enclosing said light source, said thermistor and light detector; and means for permanently connecting said light source and said light detector to said first and second optical fibers, respectively.

4. The device according to claim 3, wherein said connecting means comprises epoxy cement.

5. The device according to claim 1 wherein the optical fibers each have a diameter substantially in the range of 40 um/50 um to 400 um/500 um.

6. The device according to claim 1 wherein the shell is metal.

7. The device according to claim 1 wherein the two sections of the thin plate are arranged at an angle slightly larger than 90° one to the other.

8. The device according to claim 1, said device further including a catheter having an inside diameter and in which said optical fibers are disposed, wherein said shell has an inside diameter and the fiber holder is a rigid protective material having an outside diameter substantially the same as the inside diameter of the shell of the pressure sensing mechanism and the inside diameter of the catheter.

9. The device according to claim 1 and further including a catheter containing the optical fibers and connected to said pressure sensing mechanism, wherein the shell has a proximal portion and the fiber holder has a proximal portion, and a distal end situated within the proximal portion of the shell, and the proximal portion of the fiber holder is situated within the catheter.

10. The device according to claim 1 and further including a catheter, wherein the optical fibers are situated within the catheter.

11. The device according to claim 1 wherein the membrane comprises a thin wall of stretchable waterproof material.

12. The device according to claim 11 wherein the membrane comprises silicon rubber material in the shape of tubing.

13. The device according to claim 1 wherein said shell has a distal tip sealed with a plastic potting compound.

14. The device according to claim 1 wherein the shell has an exterior surface and further comprising a thin plastic coating situated over the exterior surface of the shell leaving the side window of said shell exposed.

15. The device according to claim 1 wherein said other section of said plate situated within the window is arranged for displacement transversely of the longitudinal direction of the shell, in response to an applied blood pressure, and said reflector section is arranged for displacement in the longitudinal direction of the shell in response to transverse displacement of said other section of the plate in the window such that the produced light emitted from the first optical fiber is reflected by the reflector section and received and measured by the means for receiving and measuring a reflected light, the amount of said reflected light varying in accordance with the amount of applied blood pressure.

16. The device according to claim 1, wherein said means for producing a light includes a light source and an A.C. driving means connected to said light source for providing an A.C. signal for driving said light source.

17. A device for the measurement of the blood pressure of a patient which comprises:
(a) means for producing a light for transmission through an optical fiber;
(b) means for receiving and measuring the light reflected through an optical fiber;
(c) a fiber holder having a proximal end;
(d) a catheter connected to the proximal end of the fiber holder;
(e) a first optical fiber, disposed in the catheter, for transmission of the produced light and having a distal end arranged longitudinally in the fiber holder and a proximal end connected to the means for producing a light;
(f) a second optical fiber, disposed in the catheter, for the transmission of the reflected light and having a distal end arranged longitudinally in the fiber holder and a proximal end connected to the means for receiving and measuring a reflected light;
(g) a pressure sensing mechanism connected to said fiber holder comprising a cylindrically shaped outer shell having an exterior surface, a distal tip, and a side window; and a thin plate having tow sections including a reflector section arranged at an angle of slightly larger than 90° to the other section, said other section being movably situated within said window and one end of the reflector section being attached to the outer shell opposite to said window, said reflector section being located a predetermined nominal distance from and perpendicular to the distal ends of said optical fibers such that the reflector section reflects light emitted from the first optical fiber into the second optical fiber in dependence of a variation in distance between the reflector section and the distal ends of said optical fibers;
(h) a membrane surrounding said shell to seal the pressure sensing mechanism and to permit the transmission of the blood pressure to the plate; and
(i) a plastic coating situated over the exterior surface of the shell leaving the side window of said shell exposed.

18. The device according to claim 17 wherein said other section of the plate situated within the window is arranged for displacement transversely of the longitudinal direction of the shell in response to an applied blood pressure and said reflector section is arranged for displacement in the longitudinal direction of the shell in response to transverse displacement of said other section of the plate in the window such that the produced light emitted from the first optical fiber is reflected by the reflector section and received and measured by the means for receiving and measuring a reflected light, the amount of said reflected light varying in accordance with the amount of applied blood pressure.

19. The device according to claim 17 wherein the distal tip of said shell is sealed with a plastic potting compound.

20. The device according to claim 17, wherein said means for producing a light includes a light source and an A.C. driving means connected to said light source for providing an A.C. signal for driving said light source.

* * * * *